Figure 1:
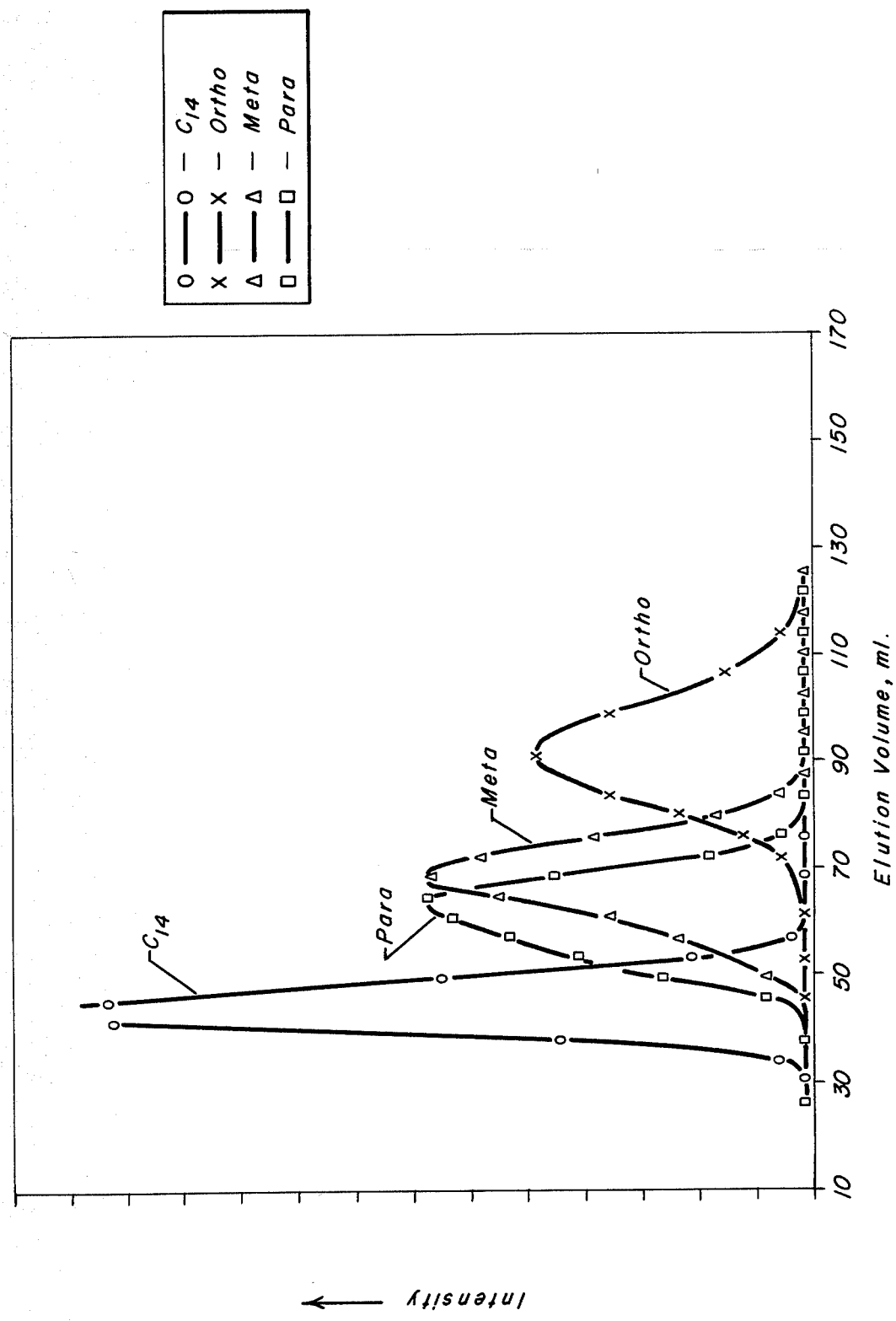

United States Patent [19]

Zinnen

[11] Patent Number: 4,620,047
[45] Date of Patent: Oct. 28, 1986

[54] PROCESS FOR THE SEPARATION OF ORTHO-NITROTOLUENE

[75] Inventor: Hermann A. Zinnen, Evanston, Ill.

[73] Assignee: UOP Inc., Des Plaines, Ill.

[21] Appl. No.: 661,860

[22] Filed: Oct. 18, 1984

[51] Int. Cl.$^4$ ............................................. C07C 79/10
[52] U.S. Cl. .................................. 568/939; 210/690; 210/672; 210/674
[58] Field of Search ................................ 568/924–940; 210/638, 690, 679, 670, 672, 674

[56] References Cited

U.S. PATENT DOCUMENTS

| | | | |
|---|---|---|---|
| 3,965,200 | 6/1976 | Manabe et al. | 260/645 |
| 4,270,013 | 5/1981 | Priegnitz et al. | 568/940 |
| 4,371,721 | 2/1983 | Wu | 568/939 |
| 4,395,372 | 7/1983 | Kluttz et al. | 568/939 |
| 4,418,230 | 11/1983 | Bakke et al. | 568/939 |
| 4,426,543 | 1/1984 | Schumacher et al. | 568/939 |

Primary Examiner—John F. Terapane
Assistant Examiner—T. J. Wallen
Attorney, Agent, or Firm—Thomas K. McBride; John F. Spears, Jr.; Louis A. Morris

[57] ABSTRACT

An adsorptive separation process for separating ortho-nitrotoluene from a feed mixture comprising the ortho-isomer and at least one other isomer of nitrotoluene. The process comprises contacting the feed mixture with an adsorbent comprising a type X zeolite, containing at the exchangeable cationic sites cations of metals from Group IA or IIA of the Periodic Table of Elements, selectively adsorbing substantially all of the ortho-nitrotoluene to the substantial exclusion of the remaining isomers, removing the non-adsorbed portion of the feed mixture from contact with the adsorbent, and thereafter recovering high-purity ortho-isomer by desorption with nitrobenzene.

5 Claims, 3 Drawing Figures

PROCESS FOR THE SEPARATION OF ORTHO-NITROTOLUENE

BACKGROUND OF THE INVENTION

1. Field of the Invention

The field of art to which the claimed invention pertains is solid bed adsorptive separation. More specifically, the claimed invention relates to a process for the separation of isomers of nitrotoluene from a feed mixture comprising such isomers which process employs a solid adsorbent which selectively removes the selected isomers from the feed mixture.

2. Background Information

The nitrotoluenes are important starting materials for the manufacture of dyes and explosives. Ortho-nitrotoluene, in particular, is used in the synthesis of dyes such as New Magenta. Para-nitrotoluene is used for the synthesis of Turquoise Blue.

The conventional method of separating isometric mononitrotoluenes involves complex distillation followed by crystallization procedures that are tedious and expensive to conduct.

It is known from U.S. Pat. No. 4,270,013 to Priegnitz et al. that ortho-nitrotoluene may be separated from other nitrotoluene isomers by using a type X zeolite containing at exchangeable cationic sites one cation selected from a group that includes potassium and barium. The specific desorbent materials disclosed by this reference are toluene and 1-hexanol.

I have discovered a method of employing zeolites for the separation of nitrotoluene isomers, particularly the ortho from a mixture of the isomers, which uses a specific desorbent material uniquely suitable for that separation.

SUMMARY OF THE INVENTION

It is, accordingly, a broad objective of the present invention to provide a process for the separation of ortho-nitrotoluene at high recoveries from a feed mixture comprising the orthoisomer and at least one other isomer of nitrotoluene.

In brief summary, the present invention is, in one embodiment, a process for separating ortho-nitrotoluene from a feed mixture comprising ortho-nitrotoluene and at least one other isomer of nitrotoluene. The process comprises contacting, at adsorption conditions, the mixture with an adsorbent comprising a type X zeolite containing cations of metals in Group IA and/or Group IIA of the Periodic Table of the Elements at the exchangeable cationic sites, selectively adsorbing the ortho-isomer to the substantial exclusion of the remaining isomer, removing the non-adsorbed portion of the feed mixture from contact with the adsorbent, and thereafter recovering high-purity ortho-nitrotoluene by desorption at desorption conditions with a desorbent material comprising nitrobenzene.

Other objectives and embodiments of the present invention encompass details about feed mixtures, adsorbents, desorbent materials and operating conditions, all of which are hereinafter disclosed in the following discussion of each of the facets of the present invention.

DESCRIPTION OF THE INVENTION

The type X and type Y crystalline aluminosilicates or zeolites are described as a three-dimensional network of fundamental structural units consisting of silicon-centered $SiO_4$ and aluminum-centered $AlO_4$ tetrahedra interconnected by a mutal sharing of apical oxygen atoms. The space between the tetrahedra is occupied by water molecules and subsequent dehydration or partial dehydration results in a crystal structure interlaced with channels of molecular dimension.

Thus, the crystalline aluminosilicates are often referred to as molecular sieves and separations performed with molecular sieves are generally thought to take place by a physical "sieving" of smaller from larger molecules appearing in the feed mixture. In the separation of aromatic hydrocarbon isomers, however, the separation of the isomers apparently occurs because of differences in electrochemical attraction of the different isomers and the adsorbent rather than on pure physical size differences in the isomer molecules.

In hydrated form, the preferred crystalline aluminosilicates generally encompass those zeolites represented by the Formula 1 below:

Formula 1

where "M" is a cation which balances the electrovalence of the tetrahedra and is generally referred to as an exchangeable cationic site, "n" represents the valence of the cation, "w" represents the moles of $SiO_2$, and "y" represents the moles of water. The cations may be any one of a number of cations which will hereinafter be described in detail.

Adsorbents comprising the type X structured zeolites are especially preferred for the adsorptive separation of isomers of this invention. These zeolites are described and defined in U.S. Pat. No. 2,882,244. The term "type X structured" zeolite as used herein shall include all zeolites which have general structures as represented in the above cited patent.

The type X structured zeolite in the hydrated or partially hydrated form can be represented in terms of mole oxides as shown in Formula 2 below:

Formula 2

where "M" represents at least one cation having a valence of not more than 3, "n" represents the valence of "M", and "y" is a value up to about 9 depending upon the identity of "M" and the degree of hydration of the crystal. The cation "M" may be one or more of a number of cations such as the hydrogen cation, the alkali metal cation, or the alkaline earth cations or other selected cations, and is generally referred to as an exchangeable cationic site.

The type X zeolite as employed in the present invention shall contain at exchanged cationic sites cations, as the cation "M" indicated in the formula above, included in Groups IA and IIA of the Periodic Table of Elements. Typically the type X structured zeolite as initially prepared and as used as a base material for the special adsorbent described herein is predominantly in the sodium form. This sodium cation is replaced or exchanged with other specific cations, such as those mentioned above, and, most preferably, barium and/or potassium.

Generally the base material will be in the form of particles such as extrudates, aggregates, tablets, pills, macrospheres, or granules produced by grinding any of the above to a desired size range. The type X zeolite can be present in the base material in concentrations generally ranging from about 75 wt. % to about 98 wt. % of the base material based on a volatile free composition. The remaining material in the base material generally comprises amorphous silica or alumina or both which is present in intimate mixture with the zeolite material. This amorphous material may be an adjunct of the manufacturing process of the type X zeolite (for example, intentionally incomplete purification of the zeolite during its manufacture) or it may be added to the relatively pure zeolite to aid in forming or agglomerating particles of the zeolite.

One example of a base material is commercially available nominal 1/16 inch extrudate comprising 13X zeolite and a minor amount of amorphous material as binder. This base material is primarily in the sodium form; that is, the cation represented as "M" in Formula 2 above is primarily sodium. By chemical analysis the $Na_2O/Al_2O_3$ ratio of this base material is usually about 0.7 or less and can typically be about 0.6. This, of course, is less than the $0.9\pm0.2$ indicated in Formula 2 above. Other cations such as H+ may be present, primarily as impurities, to supply the remainder of the cations needed for chemical balance and to meet the $0.9\pm0.2 Na_2O/Al_2O_3$ ratio. The silica to alumina ratio of this starting material by X-ray determination is about 2.5 and the same ratio by chemical analysis is about 2.6. Normally, the base material, whether in the extrudate or pellet form, is granulated to a particle size range of about 20–40 mesh (Standard U.S. Mesh) before the first ion exchange step is begun. This is approximately the desired particle size of the finished adsorbent.

Cationic or base exchange methods are generally known to those familiar with the field of crystalline aluminosilicate production. They are generally performed by contacting the zeolite with an aqueous solution of the soluble salts of the cation or cations desired to be placed upon the zeolite. The desired degree of exchange takes place and then the sieves are removed from the aqueous solution, washed and dried to a desired water content. It is contemplated that cation exchange operations may take place using individual solutions of desired cations to be placed on the zeolite or using an exchange solution containing a mixture of cations, where two or more desired cations are to be placed on the zeolite.

Feed mixtures which can be utilized in the process of this invention will comprise a mixture of at least two isomers of nitrotoluene, including the ortho-isomer. Mixtures containing substantial quantities of nitrotoluene may be produced by processes which are well known to the chemical arts. A typical feed mixture from a common process for the production of nitrotoluene contains about 62–63% o-onitrotoluene, 3–4% m-nitrotoluene and 33–35% p-nitrotoluene. Thus, the extract product stream of the present invention will comprise almost pure ortho-isomer and the raffinate product stream will predominately comprise para-isomer which, although contaminated with a relatively small amount of meta-isomer, would still be a commercially viable material.

To separate the ortho-isomer from a feed mixture containing the ortho-isomer and at least one other isomer of nitrotoluene, the mixture is contacted with the appropriate adsorbent comprising a crystalline aluminosilicate as discussed above and the ortho-isomer is more selectively adsorbed and retained by the adsorbent while the other isomers are relatively unadsorbed and are removed from the interstitial void spaces between the particles of adsorbent and the surface of the adsorbent. The adsorbent containing the ortho-isomer is referred to as a "rich" adsorbent—rich in the ortho-isomer.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream will contain as raffinate components all of the feed mixture isomers except the selected isomer and the extract stream will contain the selected isomer as the extract component.

Although it is possible by the process of this invention to produce high purity (98% or greater), ortho-isomer product at high recoveries, it will be appreciated that an extract component is never completely adsorbed by the adsorbent, nor is a raffinate component completely non-adsorbed by the adsorbent. Therefore, small amounts of a raffinate component can appear in the extract stream, and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed selected isomer to the concentration of a less selectively adsorbed isomer will be highest in the extract stream, next highest in the feed mixture, and lowest in the raffinate stream. Likewise, the ratio of the less selectively adsorbed isomer to the more selectively adsorbed ortho-isomer will be highest in the raffinate stream, next highest in the feed mixture, and the lowest in the extract stream.

The adsorbent can be contained in one or more chambers where through programmed flow into and out of the chambers separation of the ortho-isomer is effected. The adsorbent will be contacted with a desorbent material discussed in greater detail hereinbelow which is capable of displacing the adsorbed ortho-isomer from the adsorbent. The resultant extract stream comprising the ortho-isomer and desorbent material is subjected to a separation step so as to obtain high purity ortho-isomer. The resultant raffinate stream, if it comprises meta and para-isomers, may undergo further separation by means not described herein, or used as is in view of its reasonably high para-isomer purity because of the low meta-isomer content of the feedstock as discussed above.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Moving bed or simulated moving bed flow systems, however, have a much greater separation efficiency than fixed bed systems and are therefore preferred. In the moving bed or simulated moving bed processes, the adsorption and desorption operations are continuously taking place which allows both continuous production of an extract and a raffinate stream and the continual use of feed and desorbent fluid streams. One preferred embodiment of this process utilizes what is known in the art as the simulated moving bed countercurrent flow system. In such a system, it is the progressive movement of multiple liquid access points down an adsorbent chamber that simulates the upward movement of adsorbent contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

Adsorption and desorption conditions for adsorptive separation processes can generally be either in the liquid or vapor phase or both but for aromatic isomer separation processes employing zeolitic adsorbents, all liquid-phase operations are usually preferred because of the lower temperature requirements and the slightly improved selectivities associated with the lower temperatures. Preferred adsorption conditions for the process of this invention will include temperatures within the range of from about 70° F. to about 450° F. and will include pressures sufficient to maintain liquid phase. Desorption conditions for the process of the invention shall generally include the same range of temperatures and pressures as described for adsorption operations. The desorption of the selectively adsorbed isomer could also be effected at subatmospheric pressures or elevated temperatures or both or by vacuum purging of the adsorbent to remove the adsorbed isomer but this process is not directed to these desorption methods.

The desorbent materials used in the various known processing schemes vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and processes which are generally operated at substantially constant pressures and temperatures to insure liquid phase, the desorbent material relied upon must be judiciously selected to satisfy several criteria. First, the desorbent material must displace the adsorbed feed component from the adsorbent with reasonable mass flow rates without itself being so strongly adsorbed as to unduly prevent the extract component from displacing the desorbent material in a following adsorption cycle. Secondly, desorbent materials must be compatible with the particular adsorbent and the particular feed mixture. More specifically, they must not reduce or destroy the critical selectivity of the adsorbent for the extract component with respect to the raffinate components.

Desorbent materials should additionally be substances which are easily separable from the feed mixture that is passed into the process. In desorbing the preferentially adsorbed component of the feed, both desorbent material and the extract component are removed in admixture from the adsorbent. Without a method of separation such as distillation of these two materials, the purity of the extract component of the feedstock would not be very high since it would be diluted with desorbent. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

It is my belief that the desorbent materials specifically disclosed in aforementioned U.S. Pat. No. 4,270,013 to Priegnitz et al., i.e., toluene and 1-hexanol, although perfectly adequate for use as solvents in the static test procedure exemplified in that patent, would not be the most practical desorbent materials to use commercially, such as in a simulated moving bed process. I have observed that toluene when used alone as a desorbent material, will effect desorption far too slowly. Although 1-hexanol is an effective desorbent, I have reason to suspect that it, as well as other alcohols, will eventually contribute to the deactivation of zeolitic adsorbents by forming chemical reaction products which adhere to the adsorbents, resulting in their deactivation.

I have discovered nitrobenzene to be the most effective desorbent material for the separation of the present invention. Nitrobenzene, unlike toluene alone, achieves an ideal rate of desorption, and, unlike 1-hexanol, nitrobenzene exhibits no tendency to deactivate the adsorbent. The nitrobenzene is best used with a solvent, such as toluene, to control the rate of desorption, with the concentration of nitrobenzene in the nitrobenzene/toluene solution being from about 10 vol. % to about 75 vol. %.

The adsorbents used in the process of the present invention can be better understood by brief reference to certain adsorbent properties which are necessary to the successful operation of a selective adsorption process. It will be recognized that improvements in any of these adsorbent characteristics will result in an improved separation process. Among such characteristics are: adsorptive capacity for some volume of an extract component per volume of adsorbent, the selective adsorption of an extract component with respect to a raffinate component and the desorbent material, sufficiently fast rates of adsorption and desorption of the extract component to and from the adsorbent; and, in instances where the components of the feed mixture are very reactive, little or no catalytic activity for undesired reactions such as polymerization and isomerization.

A dynamic testing apparatus may be employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a non-adsorbed paraffinic tracer (n-$C_{14}$) and of isomers of nitrotoluene, all diluted in desorbent, is injected for a duration of several minutes. Desorbent flow is resumed, and the tracer and the isomers are eluted as in a liquid-solid chromatographic operation. The effluent is collected in fractions and analyzed using chromatographic equipment and traces of the envelopes of corresponding component peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate.

Selectivity, (B), with regard to two given components, is equal to the quotient obtained by dividing the respective retention volumes of such components. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1.0, it is preferred that such selectivity be greater than 2.0. Like relative volatility, the higher the selectivity the easier the separation is to perform. Higher selectivities permit a smaller amount of adsorbent to be used. The rate of exchange relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

It is also necessary that the adsorbent possess little or no catalytic activity toward any reaction such as polymerization or isomerization of any of the feed components. Such activity might effect adsorbent capacity or selectivity or product yields, or all of these, but in the adsorptive separation of aromatic hydrocarbon isomers with a zeolite-containing adsorbent this is generally not a problem. The problem may arise via the choice of desorbent material.

The example shown below is intended to further illustrate the process of this invention and is not to be construed as unduly limiting the scope and spirit of said process. The example presents test results for various adsorbent and desorbent materials when using the above dynamic testing apparatus.

EXAMPLE

In this example, tests were run with three different adsorbents, but all using a desorbent material comprising 15 vol. % nitrobenzene in toluene. In the first two runs the adsorbents were potassium exchanged X-zeolite and potassium plus barium exchanged X-zeolite, respectively. In the third run the adsorbent used was calcium exchanged Y-zeolite. All adsorbents were bound in a clay matrix. In each test the feed pulses comprised 0.5 gm. each of ortho, meta and para nitrotoluene, 0.5 gm. of normal -$C_{14}$ tracer, all in 3.0 gm. of desorbent material.

Figure 2:
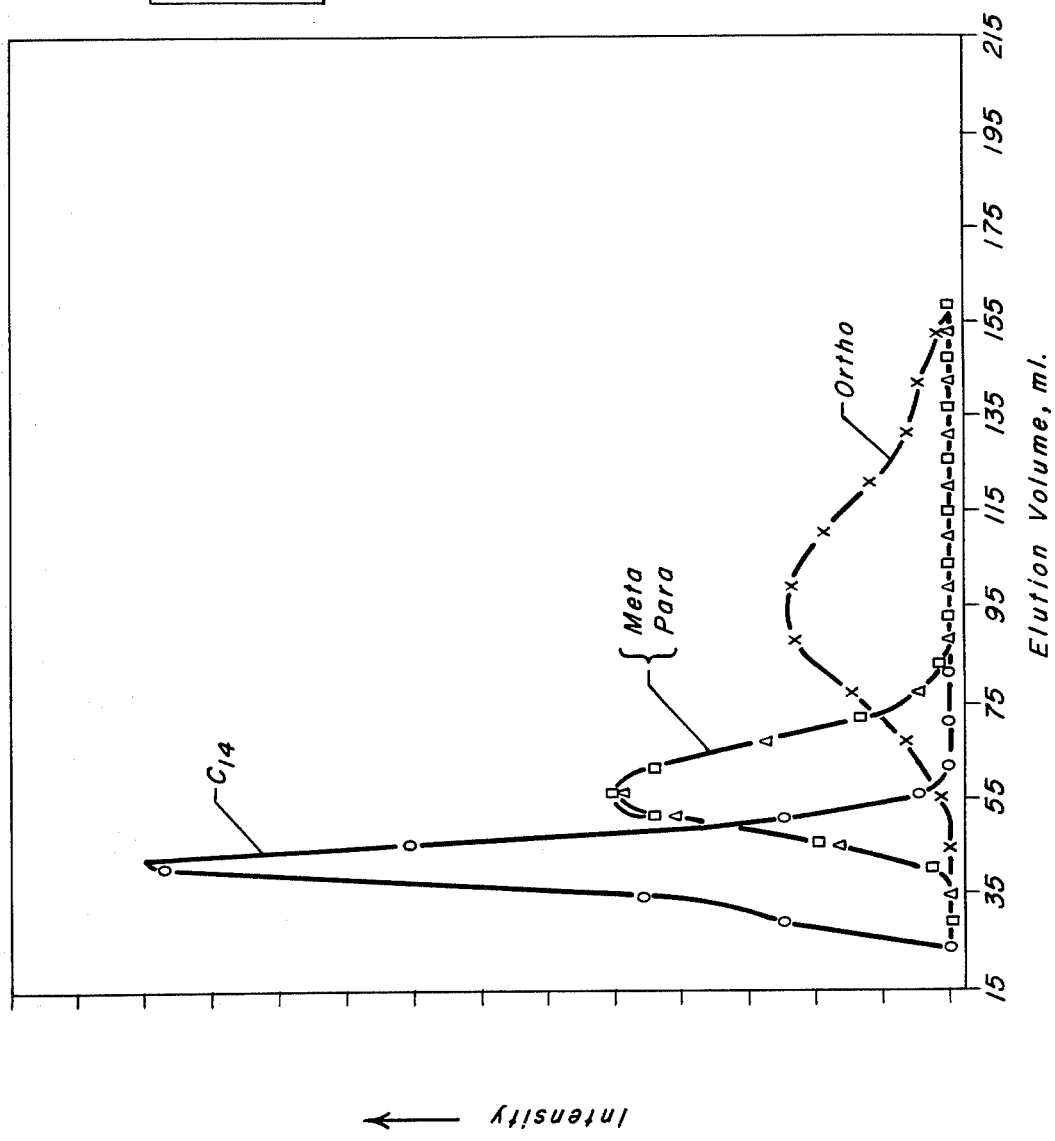
Figure 3:
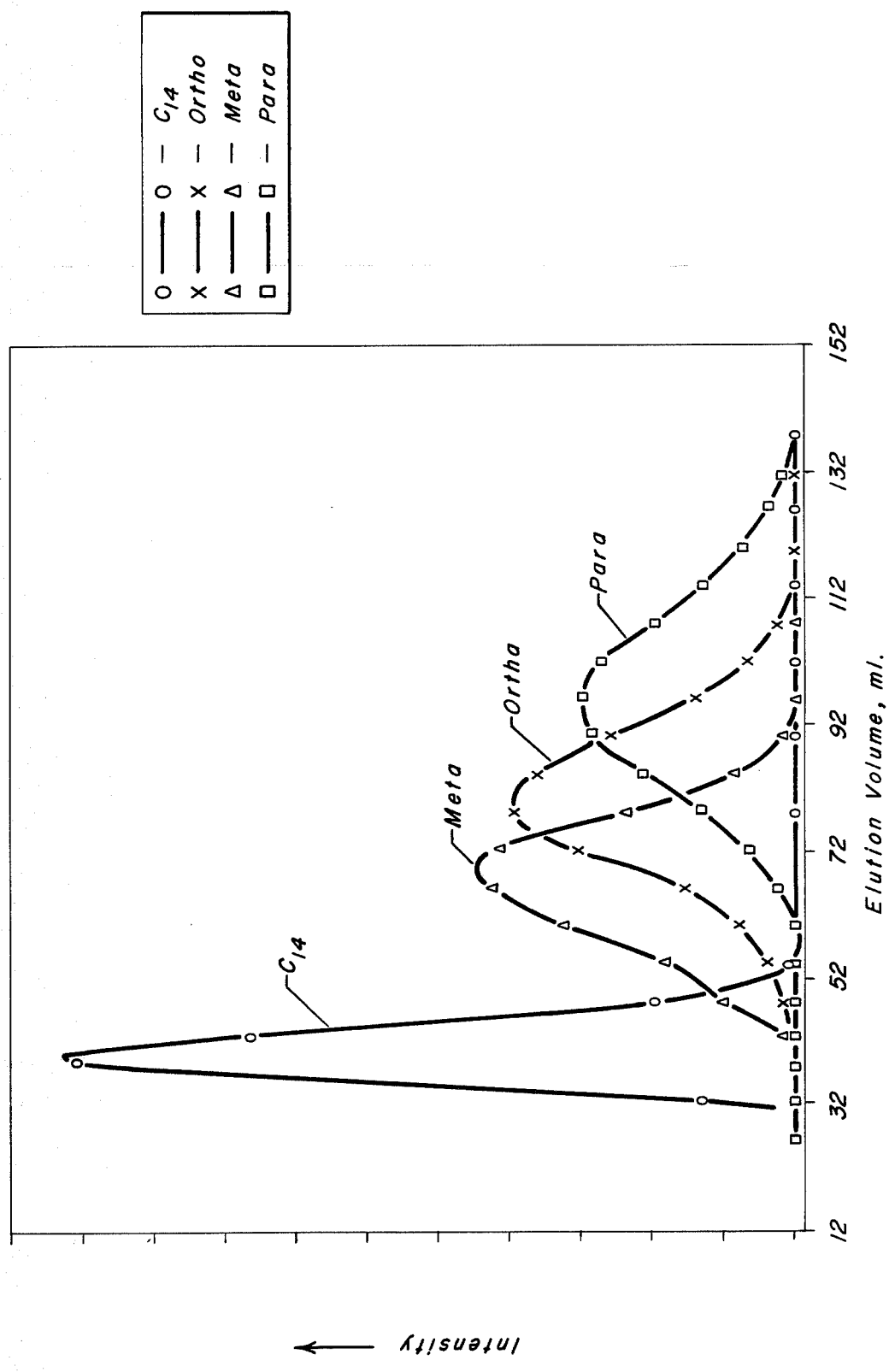

The chromatographic tracings generated in the three tests are shown in FIGS. 1, 2 and 3, respectively. In FIGS. 1 and 2, which reflect adsorbent/desorbent combinations of the present invention, almost perfect separations are achieved as indicated by the ortho-isomer being the last component to elute with almost no overlap with the curves of the other components. In FIG. 3 an adsorbent outside the scope of the present invention is employed, and the separation obtained inadequate for any commercial purpose. The widths of the peak envelopes in FIGS. 1 and 2 indicate completely acceptable rates of desorption.

Selectivities calculated from the elution curves of FIGS. 1, 2 and 3 are given in the following Table.

TABLE

| Adsorbent | Desorbent | $B_{o/m}$ | $B_{o/p}$ | $B_{p/m}$ |
|---|---|---|---|---|
| K—X | 15% nitrobenzene | 2.01 | 2.93 | 1.45 |
| BaK—X | 15% nitrobenzene | 3.35 | 3.35 | 1.00 |
| CaY | 15% nitrobenzene | 1.49 | 0.74 | 2.01 |

The Table indicates essentially ideal selectivities for the separation of ortho-nitrotoluene from the other isomers when using adsorbent/desorbent combinations of the present invention.

I claim as my invention:

1. A process for separating ortho-nitrotoluene from a feed mixture comprising ortho-nitrotoluene and at least one other isomer of nitrotoluene, which process comprises contacting at adsorption conditions said mixture with an adsorbent comprising a type X zeolite having cations comprising cations of metals in Group IA or Group IIA of the Periodic Table of the Elements at exchangeable cationic sites, selectively adsorbing said ortho-isomer to the substantial exclusion of the remaining isomers, removing the non-adsorbed portion of the feed mixture from contact with the adsorbent, and thereafter recovering high-purity ortho-nitrotoluene by desorption at desorption conditions with a desorbent material comprising nitrobenzene.

2. The process of claim 1 wherein said feed mixture contains para-nitrotoluene, meta-nitrotoluene and ortho-nitrotoluene.

3. The process of claim 1 further characterized in that said cations comprise cations of barium or potassium.

4. The process of claim 1 wherein said adsorption and desorption conditions include a temperature within the range of from about 70° F. to about 450° F. and at a pressure sufficient to maintain liquid phase.

5. The process of claim 1 wherein said separation is effected by means of a simulated moving bed flow scheme.

* * * * *